United States Patent [19]

Messing et al.

[11] 4,149,937

[45] Apr. 17, 1979

[54] HIGH SURFACE LOW VOLUME YEAST BIOMASS COMPOSITE

[75] Inventors: Ralph A. Messing, Horseheads; Robert A. Oppermann, Painted Post, both of N.Y.

[73] Assignee: Corning Glass Works, Corning, N.Y.

[21] Appl. No.: 918,794

[22] Filed: Jun. 26, 1978

Related U.S. Application Data

[63] Continuation-in-part of Ser. No. 833,277, Sep. 14, 1977, abandoned.

[51] Int. Cl.² .............................................. C12B 1/00
[52] U.S. Cl. ........................................ 195/57; 195/53; 195/54; 195/56; 195/116
[58] Field of Search ............ 195/116, 63, 68, DIG. 11, 195/52, 53, 54, 57, 59, 60, 28 R, 115

[56] References Cited

U.S. PATENT DOCUMENTS

| | | | |
|---|---|---|---|
| 3,616,246 | 10/1971 | Cherry | 195/81 |
| 3,850,751 | 11/1974 | Messing | 195/63 |
| 3,875,008 | 4/1975 | Yoshino et al. | 195/63 |
| 3,892,580 | 7/1975 | Messing | 106/41 |
| 3,983,000 | 9/1976 | Messing et al. | 195/63 |
| 4,001,085 | 1/1977 | Keyes | 195/68 |
| 4,071,409 | 1/1978 | Messing et al. | 195/63 |

FOREIGN PATENT DOCUMENTS 979547 12/1975 Canada ................................. 195/116

OTHER PUBLICATIONS

Methods in Enzymology, vol. 44, pp. 148–159, (1976).

*Primary Examiner*—Lionel M. Shapiro
*Attorney, Agent, or Firm*—William E. Maycock; Clinton S. Janes, Jr.

[57] ABSTRACT

Immobilized microbe composite comprising a porous, high surface area inorganic support having a controlled population of yeast cells bonded to the internal surfaces of the pores, the support being water insoluble, non-toxic to the cells, and having a controlled porosity such that at least 70% of the pores, on a pore size distribution basis, have a pore diameter at least as large as the smallest dimension of the cells but less than about four times the largest dimension of the cells. The composites are especially useful in situations requiring a high biomass surface within a relatively small volume.

24 Claims, 2 Drawing Figures

HIGH SURFACE LOW VOLUME YEAST BIOMASS COMPOSITE

RELATED APPLICATION

U.S. Pat. Application Ser. No. 833,278, filed Sept. 14, 1977, in the names of R. A. Messing and R. A. Oppermann, entitled "High Surface Low Volume Biomass Composite". The present application is a continuation-in-part of Application Ser. No. 833,277, filed Sept. 14, 1977, now abandoned.

BACKGROUND OF THE INVENTION

1. Field

This disclosure is concerned generally with the attachment and growth of yeast cells on inorganic surfaces. Specifically, the disclosure is concerned with providing a porous inorganic support for the immobilization of a controlled population of such cells.

2. Prior Art

The preparation and use of composites consisting of microbes (bacteria, yeast cells, etc.) fixed on the surfaces of support materials is very old and well known. Typically, a film or slime of microbes is allowed to grow over the surfaces of the support. The resultant film provides a biomass which, depending on the microbes involved, can be used in various practical applications. For example, one of the earlier trickling filter fermentation systems involved using wood shavings or other supports as a packing material which was placed in a container such as a barrel. A liquid raw material was allowed to trickle through the packing and, in some cases, air was allowed to pass upward through the packing. As the liquid was circulated with a simple pump, a film of microbes would form on the surfaces of the packing, thereby resulting in a relatively large accumulation of useful biomass which, depending on the type of microbial film (anaerobic or aerobic conditions), could be used to ferment sugars to alcohol (anaerobic) or convert alcohol to acids (aerobic). The latter process could be used to make vinegar. Early trickling filter systems of that type were commonly referred to as Schuetzenbach generators.

Numerous variations of that type of fermenting system are well known. See, for example, U.S. Pat. No. 454,586 to Bachmann which describes a fermenting vat for the fermentation of sugar solutions to a variety of products. The system consists of a flow-through vat containing a porous packing material. In that patent it was pointed out that the fermentation "germs" of a liquid substrate appeared to multiply more rapidly within the pores and on the surfaces of the packing than when the "germs" were freely floating in the liquid.

Other microbe support systems describing the use of high surface area microbe supports are shown in U.S. Pat. No. 2,440,545 (saw dust, alfalfa chops, cut straw, glass beads, stone grit, etc.); U.S. Pat. No. 3,709,364 (use of sand particles for sewage treatment); U.S. Pat. No. 3,402,103 (series of baffles in a flow through reactor upon which bacterial films are formed); and Indian Pat. No. 43542 (use of porous particles of pumice as supports for yeast cells). From a sampling of the prior art, it is quite clear that others have long appreciated certain advantages of using porous, high surface area inorganic materials as supports for microbial films.

While it can be readily appreciated that there exists a relationship between the porosity of a given support material and the useable surface area that the material provides in a given application, we have now found, quite surprisingly, that in the case of porous supports for yeast cells, there exists a range of pore sizes which, vis-a-vis the cell size, provides an extremely large surface but low volume for a high biomass concentration. Details of our findings and the immobilized yeast cell composites resulting therefrom are described in detail herein.

SUMMARY OF THE INVENTION

Our immobilized yeast cell composites comprise a porous, high surface area inorganic support material having a controlled population of yeast cells bonded to the internal surfaces of the pores, the support being water-insoluble, non-toxic to the microbes, and having a controlled porosity such that at least 70% of the pores, on a pore size distribution basis, have a pore diameter at least as large as the smallest dimension of the cells but less than about four times the largest dimension of the cells. Such composites provide a relatively large biomass surface within a relatively small volume. In preferred embodiments, the population of yeast comprises a single species of yeast cells and the inorganic support comprises material in which pore size distribution can be readily and economically controlled (e.g. amorphous or glass materials such as fritted glasses, or crystalline materials such as cordierite-like materials, etc.), and the average pore diameter of the inorganic support, for the majority of composite combinations, ranges from about 1 to about 140 microns.

SPECIFIC EMBODIMENTS

Figure 1:
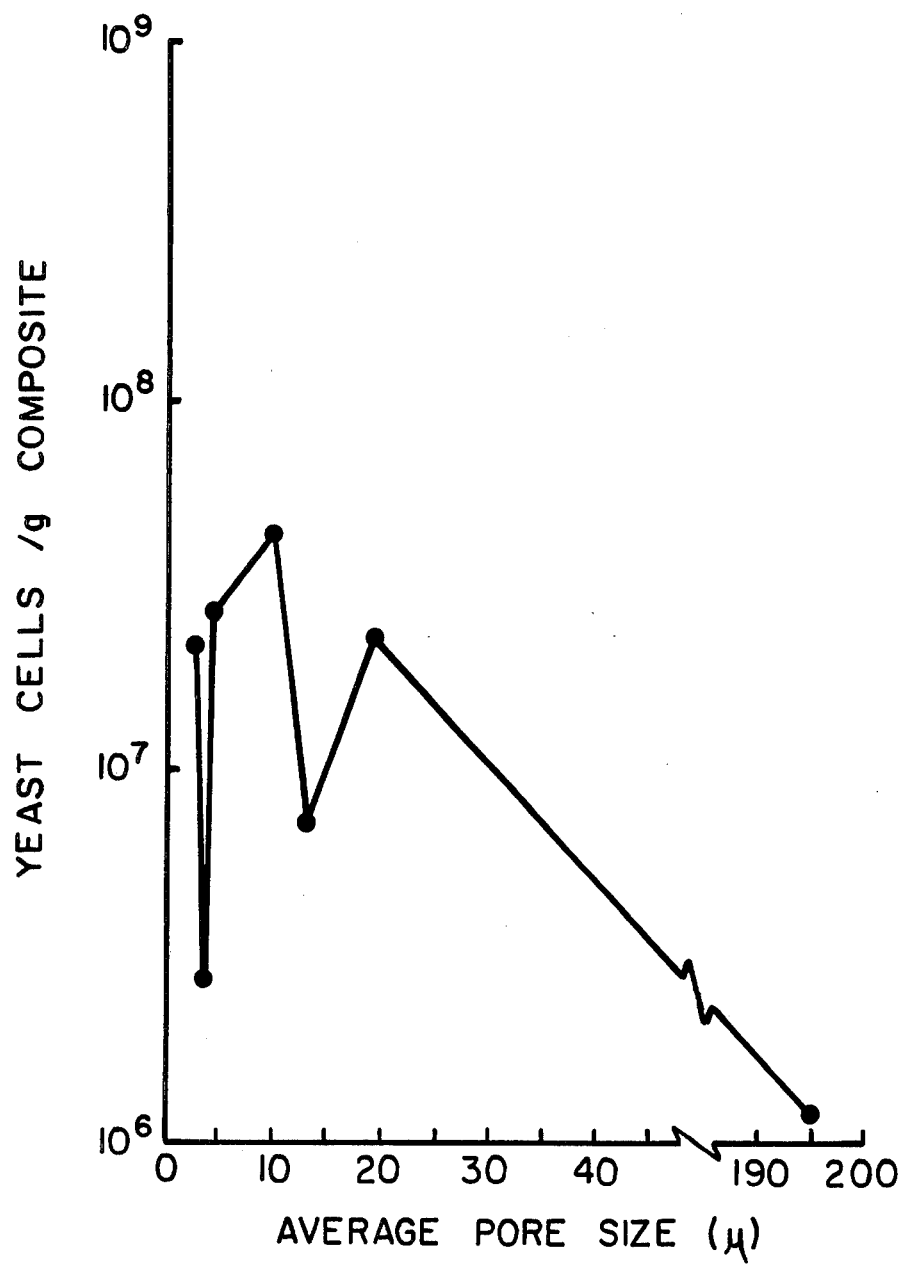
FIG. 1 is a graph illustrating the relationship between the average pore diameter of inorganic supports and the number of yeast cells bonded thereto by adsorption.

The importance of accumulating very large biomass surfaces in a limited reaction volume can be appreciated by considering some of the practical applications of immobilized microbes in general. It is well known, for example, that the mere multiplication of microbial cells can be a basis for the rapid generation of proteinaceous matter. By providing optimum conditions favoring microbial cell reproduction on a continuous basis, the accumulated cells can, under some conditions, be processed for their protein value. This is the basis for so-called single cell protein technology (SCP).

Although SCP production is presently available on a continuous (cf. batch) basis using systems known as chemostats or turbidostats, it can be appreciated that, except for wall effects, the bulk of the reproducing cells are merely suspended in a nutrient medium. Although there are certain advantages in those systems, the flow rates (or SCP production rates) are limited by that rate above which there begins to occur a washout of the microbial seed material. Very simply stated, washout refers to a situation where, because of high flow rates of nutrients through a continuous system, the loss of microbes within the reactor is greater than the gain due to cell reproduction.

Both chemostats and turbidostats are subject to washout, thus placing an upper limit on microbe production rates. Since immobilized microbes having a high amount of biomass surface per unit volume would not be as subject to high-flow rate washout as chemostat-type systems, the value of such an immobilized system becomes readily apparent, provided cellular requirements such as nutrients, waste removal, pH, oxygen supply, etc., can be satisfied.

The value of having a high biomass surface area per unit volume is also apparent in that area of fermentation concerned with the production of secondary metabolites. For example, since secondary metabolites are generally produced in the stationary phase of microbial life cycle processes, and since the total amount of secondary metabolites produced thereby will depend on the amount of biomass surface available to release the metabolites on a continuous basis, it is clear that any system which provides a means for providing and prolonging the stationary phase of a high biomass surface will provide an ideal secondary metabolite production system. As in the case of SCP production, the retention of a large biomass surface in a given volume through which nutrients can flow at high rates also permits the rapid removal of metabolic waste products as well as useful products. Our system can also be used for primary metabolite production.

Yet another area in which the technology of this disclosure has application is the field of analytical microbiology where there are clear advantages in having available immobilized microbe composites capable of uniform delivery of a stable yeast population. The composites of this disclosure can thus be used as yeast cell standards which provide a reliable and convenient method of storing and handling large quantities of yeast cells per unit volume.

Our present disclosure is grounded on our observation that there exists a unique physical relationship between a given population of microbial cells which reproduce by budding (primarily yeast cells) and a porous support material upon which the microbes form a film such that it is possible to achieve a maximum amount of biomass surface with a minimum amount of immobilized microbe volume. To a very limited extent this observation is somewhat similar to that associated with immobilized enzyme technology wherein it has been shown that there exists a relationship between the amount of active enzyme that can be loaded on a given weight (or volume) of porous support material. See for example, U.S. Pat. No. 3,850,751, which discloses an optimum support pore size range of about 100 Å to 1000 Å for most immobilized enzyme systems. This disclosure is also similar in principle to the disclosures in our pending application, cited above, wherein we have shown unique relationships exist between the pore sizes of supports and microbes which reproduce by fission (e.g. bacteria).

It should be understood that in this application our findings are applicable only to immobilized microbe composites in which the microbes reproduce by budding and our composites exclude those microbes which reproduce by other means (mycelial growth, fission, etc.). Hence, as used herein, the expressions yeast or yeast cells refers to those microbes (primarily yeasts) which reproduce by budding.

It should also be understood that for reasons discussed herein, the support or carrier material should be inorganic rather than organic.

An inorganic carrier material has a variety of marked advantages. The first is that microbes do not readily attack inorganic materials since their nutrient requirements are primarily focused to carbon and nitrogen containing materials. Organic carriers such as carbohydrates, proteins, etc. are readily attacked not only by the microbes but also by the extracellular enzymes that are elaborated by the organism. As the organic carrier is destroyed, the accumulation of microbes is reduced. In addition to durability, the inorganic carrier has the advantage of dimensional stability when contrasted to most organic carriers. By retaining the pore morphology under a variety of pressure and flow conditions, the yeast cells are protected from deformation and subsequent lysing. Again, this is an advantage in terms of biomass accumulation.

An additional advantage of an inorganic carrier is its relatively high density. Most organic materials have densities in the neighborhood of 1.0 or less while most of the inorganic materials have densities greater than 2.0. Under these circumstances, an inorganic material having an equal porosity with an organic material on a mass basis would occupy a lesser volume; therefore, on a volume basis the inorganic material could concentrate a greater biomass. The higher density inorganic materials have additional advantages in that lower pressure drops are experienced in plug-flow reactors and will perform better in a fluidized bed reactor since the particles will not flow to and remain at the surface, but, rather, they will continuously be agitated within the body of the solution.

A further advantage associated with the use of inorganics as yeast cell supports, especially according to the present disclosure, is that controlled porosity of the support can be obtained relatively simply and economically using commonly available starting materials.

Although there exists information about how yeast cell films are formed over the surfaces of supports, less information appears to exist about the actual mechanism by which the cells actually attach to the support. It is known, however, that yeast cells will attach to and reproduce on all but the most toxic substances. As used herein, the expression "bonded", when applied to the mode of attachment of the cells or yeast film to the support, includes all modes of attachment whether by physical or chemical bonds or both. In some of the examples below, microbes were simply allowed to bond to the support by what appeared to be adsorptive forces. In other cases, residues of polyisocyanates or silane coupling agents may be used to coat the surfaces of the support, thereby providing a possible basis for chemical bonding of the cells to the support via the coatings. The cells may also be crosslinked in place over or on the support surfaces.

The controlled population of microbes includes yeast cells of a given species, all being in the same general size range as well as other collections of yeast cells having a similarity of sizes such that at least 70% of the pores of the support have pore diameters large enough to readily admit substantially all members of the population and, for purposes of maintaining maximum usable surface area and protection against yeast cell washout, less than about four times the maximum dimension of the yeast cells.

The smallest and largest major dimensions of most yeast cells can be found in textbooks or can be determined using known techniques. Whether at least 70% of the pores of a given inorganic support have pore diameters equal to one to about four times the largest yeast cell dimension can be determined by known means such as via mercury intrusion porosimetry distribution technique. All such supports should have a high surface area. As used herein, the expression high surface area refers to a support having a surface area greater than about 0.01 m²/gram.

The rationale for the dimensions of the optimum pore size range can be expressed as follows: The relationship between the pore morphology and the accumulation of a major biomass is dependent upon mode of reproduction of the organism. In the case of yeasts, which reproduce by budding, the following example can be used: *S. cerevisiae* has an average dimension of 2.5–6.5 by 4.5–9.5 microns, (The Yeasts, a Taxonomic Study, edited by J. Lodder, Second Printing, 1971, North Holland Publishing Company, Amsterdam-London). It can be seen that when cells on either side of the pore begin to bud they will increase their length by approximately ¼ to ½ their original length. This produces cells on opposite sides of the channel requiring pores approximately 3 times the cell's total length. Now, if a third cell is to pass the two fixed on the walls, a proper channel must be left which would be approximately one more major cell dimension. Therefore, to allow passage and immobilization of yeast in any state, we must make use of pores of approximately 4 times the maximum dimension of the yeast cell used. There are biological variations within species so that all the organisms are not, in fact, of a particular size and one will note in the examples to follow there are variations shown within the cultures which produce several optimum peaks indicating optimum loading for that particular segment of the population.

Therefore, while it can be appreciated that the pore diameter of the support should be at least as large as the smallest dimension to readily admit the yeast cells, a higher loading of microbes or a more effective utilization of the largely internal surface area occurs when the pores are somewhat larger than the minimum size needed to readily admit the cells. We have found that the upper limit of pore size which in general permits the most effective utilization of surface area per unit volume of support is about four times the largest major dimension of the yeast cell bonded therein.

It should be noted that in some cases where yeast cell reproduction per se is not of prime concern (e.g. secondary metabolite production where a relatively constant stationary phase is desired), a more effective utilization of internal surface area results when the bulk of the pores are closer in size to the smallest dimension of the yeast cell. Thus, in general, depending on the purpose for which the cells are to be immobilized, it can be appreciated that, in general, the most efficient use of surface area for bonding a given population of microbes results when a majority (at least 70%) of the pores of a porous inorganic support have pore diameters ranging in sizes equal to the smallest microbe dimension to about four times the largest dimension. As shown in the examples below, it was found that the peak value for biomass surface accumulation was found when the support pore size was within that range. Specifically, optimal loading results were obtained when at least 70% of the pores had pore diameters about three to four times the smallest major microbe dimension.

The importance of controlling pore size distribution of the porous inorganic support was observed by comparing the biomass loading results obtained with separate porous supports, only one of which had a tightly controlled pore size distribution. In general, the experimental results appeared to indicate that at least about 70% of the pores should have pore diameters at least as large as the smallest dimension of the microbe but less than about four times the largest major dimension.

In the examples below, the porous supports having a known and reasonably controlled porosity included various fritted glass materials and cordierite-like crystalline materials. The best fritted glass and cordierite supports had at least 70% of their pore sizes within the required range (e.g. 77–100% for the fritted glass, and 76–100% for the $Al_2O_3$-cordierite). The pore size ranges in microns, (with average pore sizes in parentheses) for the support materials were as follows: fritted glasses 1.5–4.5 (3.5), 3–6 (4.5), 8–20 (13), 18–100 (40), and 170–220 (195); cordierite-like materials 1.5–6 (3) and 2–19 (10); and spinel-zirconia material 17–35 (19).

Because our yeast loading (biomass) determinations involved measuring the number of microbes bonded within the pores of the various porous supports, we could not use conventional plate counting techniques. Instead, the microbe counts were determined using a DuPont Biometer Model No. 760 which determines microbe count based on the amount of ATP present in a given sample. The actual procedure used was as follows: To approximately 10–20 mg of composite add 0.5 ml of 90% DMSO (Dimethylsulfoxide) in water. Mix the suspension vigorously for 10 seconds. Allow the suspension to stand 20 minutes, then add 4.0 ml of pH 7.4 0.01M MOPS (Morpholinopropane sulfonic acid) buffer. Mix vigorously and store in ice until it is to be read in the biometer. 10 $\mu$l of this solution is added to a cuvette already in the biometer which contains the luciferin-luciferase mixture. The extracted ATP reacts with the enzyme mixture to produce light which is determined quantitatively and is proportional to the amount of ATP.

The reliability of the results using the above technique is ±20%. Further information concerning the use and reliability of the Biometer measuring technique can be found in the following publication: Instruction Manual, 760 Luminescence Biometer, E. I. DuPont De Nemours & Co., Instrument Products Division, Wilmington, Del. 19898, December 1970.

Our findings and specific methods of making the composites of the present invention are illustrated in the examples below. The microbes bonded to the various supports by the indicated techniques included the yeast cells *Saccharomyces cerevisiae* and *S. amurcae*. Unless otherwise indicated, the support materials were in particulate form having a particle size in the range of 18–25 mesh, U.S. Standard Sieve.

EXAMPLES

The yeast cells used as an example of this invention were all grown in shake flasks in nutrient broth plus 1% dextrose for a period of 36–40 hours at room temperature. The cell suspension was centrifuged and washed three times with a sodium-potassium phosphate buffer at a pH of 7.2. The washed, concentrated suspension was added to the carrier and mixed by shaking for 3 hours of contact time.

For absorption, the carrier (inorganic support) was ground to an 18–25 mesh, sterilized dry, and placed in a 37° C. incubator overnight to produce a dry carrier. 0.5 gram of each carrier was used in a 50 ml micro Fernbach flask. 10 ml of the concentrated yeast cell suspension was added per flask. At the end of 3 hours contact time, the excess cells were poured off, the carrier was washed 3 times with phosphate buffer and stored in the refrigerator.

For the coupling procedure, 0.5 gram of each carrier was placed in a 50 ml micro Fernbach flask, autoclaved dry, and placed in a 37° C. incubator overnight to dry the carrier. 10 ml of a 0.5% solution of PAPI 901 (a commercially available polyisocyanate) in acetone was added to each flask. The flasks were shaken for ¾ of an hour and the PAPI solution poured off. 10 ml of the concentrated yeast cell suspension was then added to each flask and the flask was then shaken for 3 hours contact time. After the 3 hour period the excess cells were poured off and the carrier washed 3 times with phosphate buffer. All the flasks were stored overnight at refrigerator temperatures.

Determinations of the number of yeast cells on the carrier were performed by use of the DuPont Biometer. As indicated above, this apparatus determines the amount of ATP in a sample. The ATP from the yeast cells on the carrier was extracted by placing the carrier in an ATP solvent. Small amounts of this extract were then placed in the meter and the amount of ATP determined. A correlation was made between the amount of ATP in a yeast cell and the total numbers of yeast cells as determined by plate count. In this manner the total number of cells on the carrier could be determined.

The results of the first experiment using adsorbed cells are shown in Table I.

TABLE I

*Saccharomyces cerevisiae* Immobilized Into Various Carriers by Adsorption

| Average Pore size in Microns ($\mu$) | Pore Distribution ($\mu$) | Carrier Composition | Average Percent of Pores in Optimum (1–4x) Range | Number of Cells Per Gram of Carrier[1] |
|---|---|---|---|---|
| 3.0 | 1.5–6 | Cordierite | 74 | $2.1 \times 10^7$ |
| 3.5 | 1.5–4.5 | Fritted Glass | 81 | $2.7 \times 10^6$ |
| 4.5 | 3–6 | " | 100 | $2.7 \times 10^7$ |
| 10 | 2–19 | Cordierite | 74 | $4.3 \times 10^7$ |
| 13 | 8–20 | Fritted Glass | 95 | $7.0 \times 10^6$ |
| 19 | 17–35 | Spinel-Zirconia | 100 | $2.3 \times 10^7$ |
| 40 | 18–100 | Fritted Glass | 19 | $4.9 \times 10^6$ |
| 195 | 170–220 | " | 0 | $1.1 \times 10^6$ |
| Non-Porous | — | Borosilicate Glass | 0 | $1.9 \times 10^6$ |

[1]Determined by Dupont Biometer and recalculated as yeast cells.

From the graph (FIG. 1) it can be seen that the data presents a single fairly broad curve extending from 3 to 40 microns with two peaks. This observation correlates very well with the observation that the average cell dimensions were 4 by 5.5 microns (2.5–4 by 4–7) while 20% of the cells were 4.5 by 7 microns in length. The amount of variability within a culture accounts for the broad double peak. The sharp drop at 3.5 microns was caused not by the size of the average pore but by the smaller range of pores in that particular carrier. In this carrier the pore sizes measure from 1.5–4.5 microns while in the 3.0 micron carrier the range is 1.5–6.0 microns.

The data obtained from the experiments using chemically coupled yeast cells are presented in Table II.

TABLE II

*S. amurcae* Immobilized to Various Carriers by Chemical Coupling

| Average Pore size in Microns ($\mu$) | Pore Distribution ($\mu$) | Carrier Composition | Average Percent of Pores in Optimum (1–4x) Range | Number of Cells Per Gram of Carrier[1] |
|---|---|---|---|---|
| 3.5 | 1.5–4.5 | Fritted Glass | 69 | $6.5 \times 10^4$ |
| 4.5 | 3–6 | " | 100 | $1.8 \times 10^6$ |
| 13 | 8–20 | " | 100 | $1.2 \times 10^6$ |
| 19 | 17–35 | Spinel-Zirconia | 100 | $1.7 \times 10^6$ |
| 40 | 18–100 | Fritted Glass | 81 | $5.5 \times 10^6$ |
| 195 | 170–220 | " | 0 | $3.6 \times 10^5$ |
| Non-Porous | — | Borosilicate Glass | 0 | $9.0 \times 10^{3*}$ |

[1]Determined by DuPont Biometer and recalculated as yeast cells.
*Originally determined at $10^5$ units of ATP which is lower limit of Biometer.

Figure 2:
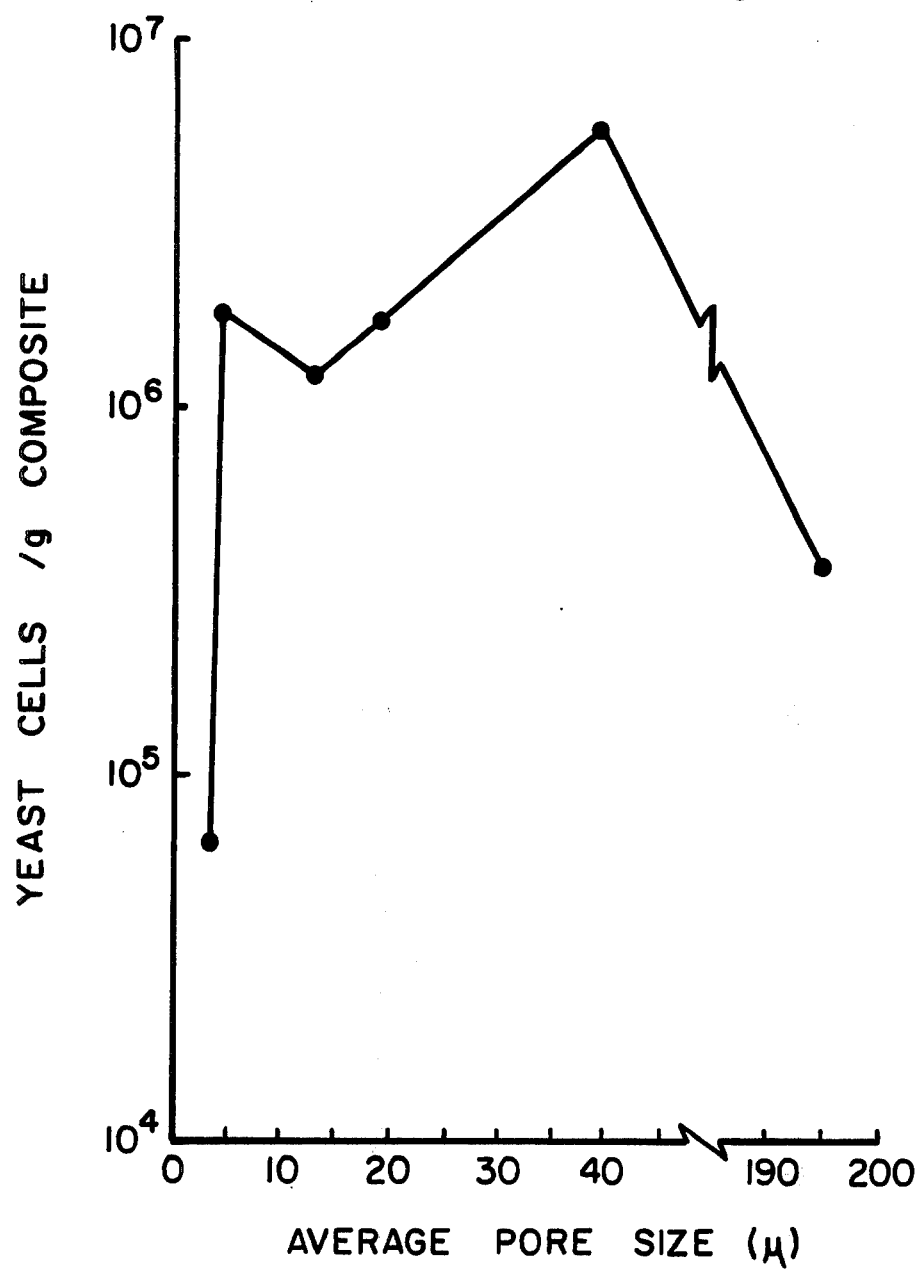
FIG. 2 is another graph illustrating the relationship between the average pore diameter of the supports and the number of yeast cells bonded thereto by chemical coupling (covalent bonds).

Here, because the culture was basically biphasic, small single cells and large duplicating double cells, the graph (FIG. 2) again shows a double peak with the major peak being in the range of 13 to 40 plus microns. This correlates well with the observation that the average small single cells were 5.5 by 7 microns (3–7 by 6–9) and that the larger double cells which constituted approximately 75% of the population, were 6–8 by 13–18 microns long.

Both experiments unequivocally show that the optimum pore size for accumulating biomass of a budding form is 1 times the smaller dimension to 3–4 times the largest dimension of that cell.

Given this disclosure, certain changes will become apparent. Hence, it is intended that the scope of the inventions discussed herein should be limited only by the following claims.

We claim:

1. An immobilized yeast composite comprising a porous, high surface area inorganic support having a controlled population of yeast cells bonded to the internal surfaces of the pores, the support being water-insoluble, non-toxic to the microbes, and having a controlled porosity such that at least 70% of the pores, on a pore size distribution basis, have a pore diameter at least as large as the smallest dimension of the cells but less than about four times the largest dimension of the cells.

2. The composite of claim 1 wherein the population of microbes comprises yeast cells of a single species.

3. The composite of claim 1 wherein the average pore diameter is in the range of about 1 to 140 microns.

4. The composite of claim 1 wherein the inorganic support comprises an amorphous material.

5. The composite of claim 4 wherein the support comprises fritted glass.

6. The composite of claim 1 wherein the inorganic support comprises a crystalline material.

7. The composite of claim 6 wherein the support comprises a cordierite-like material.

8. The composite of claim 6 wherein the support comprises a spinel-zirconia material.

9. The composite of claim 1 wherein intermediate the support surfaces and the microbes is a coating material selected from residues of polyisocyanates and silane coupling agents.

10. The composite of claim 1 wherein the yeast cells are selected from the genus *Saccharomyces*.

11. The composite of claim 10 wherein the yeast cells are in the species *cerivisiae*.

12. The composite of claim 10 wherein the yeast cells are in the species *amurcae*.

13. A method of preparing a high surface area, low volume biomass composite comprising the step of exposing an aqueous suspension of a controlled population of yeast cells to a sterilized porous inorganic support material having a porosity such that at least 70% of the pores, on a pore size distribution basis, have pore diameters at least as large as the smallest dimension of the cells but less than about four times the largest dimension of the cells, the exposure being under conditions sufficient to result in the bonding of at least some of the cells onto the internal surfaces defining the pores of the support material.

14. The method of claim 13 wherein, prior to exposure to the yeast cell suspension, the surfaces of the support are treated with a coating agent selected from polyisocyanates and silane coupling agents.

15. The method of claim 13 wherein the population of yeast cells comprises a single species.

16. The method of claim 13 wherein the average pore diameter of the support is in the range of about 1 to 140 microns.

17. The method of claim 13 wherein the support comprises an amorphous material.

18. The method of claim 13 wherein the support comprises fritted glass.

19. The method of claim 13 wherein the support comprises a crystalline material.

20. The method of claim 19 wherein the support comprises a cordierite-like material.

21. The method of claim 19 wherein the support comprises a spinel-zirconia material.

22. The method of claim 13 wherein the yeast cells are selected from the genus *Saccharomyces*.

23. The method of claim 22 wherein the yeast cells comprise *Saccharomyces cerivisiae* cells.

24. The method of claim 22 wherein the yeast cells comprise *Saccharomyces amurcae* cells.

* * * * *